United States Patent [19]

Marraccini et al.

[11] Patent Number: 5,087,765
[45] Date of Patent: Feb. 11, 1992

[54] PROCESS FOR PREPARING CHLOROTRIFLUOROETHYLENE TELOMERS AND NEW TELOMERS OBTAINED

[75] Inventors: Antonio Marraccini; Antonio Pasquale, both of Novara; Marco Vincenti, Turin, all of Italy

[73] Assignee: Ausimont S.r.L., Milan, Italy

[21] Appl. No.: 463,550

[22] Filed: Jan. 11, 1990

[30] Foreign Application Priority Data

Jan. 12, 1989 [IT] Italy .................................. 19078 89

[51] Int. Cl.⁵ .............................................. C07C 41/01
[52] U.S. Cl. ........................................ 568/677; 568/683; 568/684; 568/615; 570/134; 570/142; 570/172; 252/78.1
[58] Field of Search ............... 568/677, 683, 684, 615; 570/134, 142, 172

[56] References Cited

U.S. PATENT DOCUMENTS 4,754,085  6/1988  Gervasutti et al. ................. 568/684

FOREIGN PATENT DOCUMENTS 2148286  5/1985  United Kingdom .

*Primary Examiner*—Howard T. Mars
*Attorney, Agent, or Firm*—Stevens, Davis, Miller & Mosher

[57] ABSTRACT

In the process for preparing chlorotrifluoroethylene telomers by reaction of chlorotrifluoroethylene with $CF_3CF$ or $R_x-CF_2OF$ (wherein $R_x$ may be also a perfluoroalkyl radical having 1 to 10 carbon atoms), the content of telomers with end groups —F is increased or mixtures of telomers containing species with end groups —Cl are obtained by adding $F_2$, according to particular modalities, to the reaction medium.

11 Claims, No Drawings

PROCESS FOR PREPARING CHLOROTRIFLUOROETHYLENE TELOMERS AND NEW TELOMERS OBTAINED

BACKGROUND OF THE INVENTION

The present invention relates to a process for preparing chlorotrifluoroethylene telomers. More particularly, the invention relates to a process for preparing telomers of chlorotrifluoroethylene with perhaloalkylfluoroxy compounds. It relates also to new chlorotrifluoroethylene telomers prepared by means of said process.

U.S. Pat. No. 4,577,044 describes a new type of chlorotrifluoroethylene telomers obtained by reacting chlorotrifluoroethylene with $CF_3OF$. The following telomeric species are obtained: $F(CF_2—CFCl)_nF$, $CF_3O—(CF_2CFCl)_n—F$ and $CF_3O—(CF_2CPCl)_n—OCF_3$, wherein "n" usually ranges from 1 to 10 and the telomeric units ($CF_2—CFCl$) are randomly distributed, i.e. they can be linked both in head-to-head arrangement and in head-to-tail arrangement.

As concerns the telomeric products which are characterized, as the latter, by not high values of the telomerization degree, it is supposed that the nature of the end groups and the type of bond (namely oxygen-carbon or carbon-carbon), by which these groups are bound to the monomeric units, may remarkably affect the physical and chemical properties of the telomers, in particular owing to different bond strengths, different sizes of the groups and differences in the steric hindrance of same and in the flexibility of the bond type (oxygen-carbon or carbon-carbon).

By consequence, the telomers of chlorotrifluoroethylene with $CF_3OF$ cannot exhibit a wide range of properties as they posses only the end groups $CF_3O—$ and $F—$. Now, it is well known that an excellent property for a particular use of chlorotrifluoroethylene telomers may result in a handicap for another use.

Italian patent application No. 23179 A/87 of the present assignee filed on Dec. 23, 1987, describes a process for preparing telomers of chlorotrifluoroethylene with perhaloalkylfluoroxy compounds of formula $R_y—CF_2OF$ in which $R_y$ is a perhalogenated alkyl radical having 1 to 10 carbon atoms and containing fluorine atoms or fluorine and chlorine atoms. By this process it is possible to obtain telomers having the following end groups:

F;
perhaloalkoxy groups, for example $R_y—CF_2—O—$ or $R_y—O—$;
perhaloalkyl groups, for example $R_y—$ and $R_y—CF_2—$.

Telomer mixtures are obtained, which contain, inter alia, the following telomeric species (in each telomer, the monomeric unit $CF_2—CFCl$ is schematically represented by letter M):

$R_y—CF_2—O—(M)_n—F$
$R_y—CF_2—O—(M)_n—O—CF_2—R_y$
$R_y—CF_2—O—(M)_n—R_y$
$R_y—O—(M)_n—F$
$R_y—CF_2—(M)_n—F$
$F—(M)_n—F$

By adjusting the operative modalities it is possible to obtain, in particular, mixtures of telomers having prevailingly F and perhaloalkoxy end groups, or mixtures of telomers having, besides F and perhaloalkoxy end groups, a high proportion of perhaloalkyl end groups.

Thus, it is possible to vary, in a wide range, the distribution and the nature of the end groups contained in the telomeric species, thereby obtaining a wide range of products having different physical and chemical properties and suited to meet various applicative requirements.

It has now been found that by adding elemental fluorine to the reagents consisting of the perhalofluoroxy compound and of chlorotrifluoroethylene, it is possible, in certain conditions, to increase the proportion of telomers having one or two —F end groups.

This result is surprising since fluorine does not exert any telogenic action on chlorotrifluoroethylene: it is known in fact that, by reacting of fluorine with chlorotrifluoroethylene, an adduct is obtained, which contains from one molecule to two molecules of chlorotrifluoroethylene per each molecular of $F_2$.

It has also surprisingly been found that always by adding elemental fluorine to the reagents consisting of the perhalofluoroxy compound and of chlorotrifluoroethylene it is possible, following other operative modalities, to obtain mixtures of telomers containing species with end groups —Cl (besides chlorine which is present in the telomeric end unit $—CF_2—CFCl—$).

Therefore, the range of obtained products is broadened by the present invention.

The mixtures of telomers having an increased content of end groups —F are of interest because a lower content of perhaloalkoxy end groups, i.e. of ethereal end groups, results in a lower compressibility of the fluid.

On the other hand, the mixture of telomers containing species with —Cl end groups exhibit a lesser variation of the viscosity as a function of the temperature.

Thus, it is an object of the present invention to provide a process for preparing telomers of chlorotrifluoroethylene with perhalofluoroxy compounds which shall permit to obtain, by using particular modalities, an increased proportion of —F end groups.

Another object is to provide a process for preparing the abovesaid telomers which shall permit to obtain, by using other modalities, mixture of telomers containing species with —Cl end groups, i.e. also an increase Cl/F ratio.

Still another object is to provide new chlorotrifluoroethylene telomers having, at one end, a —Cl end group and, at the other end, a perhaloalkoxy or perhaloalkyl end group.

The first two above-mentioned objects are achieved by the process, forming the object of the present invention, for preparing chlorotrifluoroethylene telomers.

This process is characterized in that chlorotrifluoroethylene, elemental fluorine and a perhalofluoroxy compound of formula $CF_3OF$ or $R_x—CF_2OF$, in which $R_x$ is a either straight or branched perhalogenated alkyl radical, a perhaloalkylmonoetherreal radical or perhaloalkylpolyethereal radical having 1 to 10 carbon atoms, containing fluorine atoms or fluorine and chlorine atoms, are reacted at a temperature from $-100°$ to $+40°$ C.; the perhalofluoroxy compound and the elemental fluorine are fed to the reaction medium after dilution in a gas which is inert under the reaction conditions; the ratio, in N liters/hour, between elemental fluorine and perhalofluoroxy compound ranges form 0.1 to 20, while the ratio, in N liters/hour, $$\frac{\text{perhalofluoroxy compound + elemental fluorine}}{\text{inert gas}}$$

ranges from 0.01 to 1.

The inert diluting gas may be, for example, nitrogen, argon, helium or a gaseous chlorofluorocarbon selected, for example, from 1,2-dichlorotetrafluoroethane and dichlorodifluoromethane. In order to carry out the reaction, preferably a stream of gaseous or liquid perhalofluoroxy compound and of gaseous fluorine, both diluted in the inert gas, is fed to a reactor containing chlorotrifluoroethylene in the liquid state of dissolved in a solvent. More preferably, the perhalofluoroxy compound is fed in the gaseous state. If it is operated under pressure, the reaction can be conducted at a temperature higher than the boiling point of chlorotrifluoroethylene ($-27.9°$ C.). If it is operated in a solution, a chlorotrifluoroethylene solvent is used, which is inert under the reaction conditions, in particular a chlorofluorocarbon, such as, for example, 1,2-dichlorotetrafluoroethane, fluorotrichloromethane and dichlorodifluoromethane. Usually, the chlorotrifluoroethylene amount contained in the solution ranges from 20 to 80% by weight.

When mixtures of telomers having an increased content of —F end groups are to be obtained, the following modalities are employed simultaneously:

a not high ratio of $F_2$ to perhalofluoroxy compound, in N liters/hours, is used;

a rather low or very low ratio, in N liters/hour, $$\frac{\text{perhalofluoroxy compound + elemental fluorine}}{\text{inert gas}}$$

is used;

conditions, which reduce the heat amount generated in the reaction medium and promote an effective dispersion thereof are utilized.

These conditions are obtained by adopting one of the following modalities or both modalities together:

a) according to the first modality, it is operated in a lower temperature range, provided said temperatures are higher that the threshold temperature of the reaction between perhalofluoroxy compound and chlorotrifluoroethylene;

b) the second modality consists in precooling the telogen and fluorine before they are fed; if necessary, the telogen is fed in the liquid state.

Another modality which helps in obtaining these conditions consists in conducting an effective stirring in the reactor.

To obtain such telomer mixtures having an increased content of —F end groups, the following combination of modalities is preferably used:

a) the $F_2$/perhalofluoroxy compound ratio ranges from 0.1 to 10 and, more preferably, from 0.1 to 3;

b) the $$\frac{\text{perhalofluoroxy compound + elemental fluorine}}{\text{inert gas}} \text{ ratio}$$

ranges from 0.01 to 0.50 and, more preferably, from 0.03 to 0.35;

c) the reaction temperature ranges from $-100°$ to $-40°$ C. and, more preferably, from $-80°$ to $-60°$ C.

In the range of said combination of modalities, the proportion of telomers having one or two —F end groups increases as the temperature decreases and as the $$\frac{\text{perhalofluoroxy compound + elemental fluorine}}{\text{inert gas}}$$

ratio decreases.

Following the modalities which promote the formation of —F end groups, it is possible to obtain, for example, mixtures of telomers containing up to 45% by weight of $F—(M)_n—F$ telomers having a F/Cl weight ratio equal to or higher than 0.6.

When mixtures of telomers containing species with —Cl end groups are to be obtained, the following modalities are simultaneously adopted:

a high $F_2$/perhalofluoroxy compound ratio is used;

a low dilution of the perhalofluoroxy compound and of fluorine in the inert gas is used;

conditions are used, which increase the heat amount generated in the reaction medium but do not promote the dispersion thereof.

To this purpose, a reaction temperature ranging from $-75°$ to $+40°$ C. is used. A moderate stirring can be carried out too.

To obtain such mixtures of telomers containing species with —Cl end groups, the following combination of modalities is preferably used:

a) a $F_2$/fluoroxy compound ratio ranging from 2 to 20 and, more preferably, from 2 to 10, is used;

b) a $$\frac{\text{perhalofluoroxy compound + elemental fluorine}}{\text{inert gas}} \text{ ratio}$$

ranging from 0.3 to 1 is used.

c) a reaction temperature ranging from $-75°$ to $+40°$ C. and, more preferably, from $-75°$ to $-40°$ C., is used.

In the range of the abovesaid combination of modalities, the proportion of telomers having —Cl end groups increases with increasing temperature and with decreasing dilution degree of the perhalofluoroxy compound and of fluorine in the inert gas.

According to the modalities which promote the formation of —Cl end groups it is possible to obtain, for example, up to more than 80% by weight of telomers having one or two Cl end groups and having a Cl/F weight ratio equal to or higher than 0.7.

According to another aspect of the process object of the present invention, in the conditions in which it is possible to direct the telomerization reaction prevailingly towards the desired telomeric species, it is furthermore possible, by decreasing the heat amount generated in the reaction medium and by favouring an effective dispersion thereof, to direct, within certain limits, the telomerization degree towards low values. That is obtained by using low flowrates of the telogen and $F_2$ and a low temperature of the reaction medium and, optionally, by precooling the telogen and the $F_2$. Another modality which helps in obtaining this result consists in carrying out an intense stirring in the reactor. Still another modality, which cooperates in obtaining this result, consists in operating with a very low $$\frac{\text{perhalofluoroxy compound + elemental fluorine}}{\text{inert gas}}$$

ratio.

It is possible to obtain, for example, up to 80% and more of telomers having a "n" value ranging from 1 to 6.

If the fluoroxy compound is fed in the liquid state is to the reactor, it is mixed with a liquid which is inert under the reaction conditions, in particular a chlorofluorocarbon, for example 1,2-dichlorotetrafluoroethane, fluorotrichloromethane and dichlorodifluoromethane, or it is conveyed, in the form of an aerosol, with the inert gas.

To the reactor containing a solvent of chlorotrifluoroethylene it is possible also to feed a flow of elemental fluorine, inert gas and fluoroxy compound, either in the gaseous or in the liquid state, according to one of the feeding procedures indicated hereinbefore, and, separately, a gaseous or liquid chlorotrifluoroethylene flow: in this case, chlorotrifluoroethylene is preferably fed in the liquid state.

It is assumed that the mechanism of action of the fluoroxy compound as a telogen partially passes through a homolytic breaking of the O—F bond according to the scheme:

$$R_x—CF_2—OF \rightarrow R_x—CF_2—O^\bullet + F^\bullet$$

wherefore radicals $R_x—CF_2—O^\circ$ and $F^\circ$ can act as telomerization starters and terminators. It is assumed too that the abovesaid radicals can also undergo further fragmentation and re-arrangement reactions with formation of other radicalic species, which, in turn, can act as telomerization starters and terminators. In the case of radicals $R_x$ containing Cl atoms, it is assumed, moreover, that one chlorine atom or more chlorine atoms can be substituted by fluorine atoms.

Starting from a perfluorofluoroxy compound, radicals $R^1$ derived from $R_x$ are therefore formed, wherein $R_x$ having at least two carbon atoms has lost one or more carbon atoms and/or $R_x$ having at least three carbon atoms, has undergone a re-arrangement. More commonly, radical $R^1$ is a radical $R^2$ containing a lower number of carbon atoms with respect to $R_x$, wherefore when $R_x$ contains from 2 to 10 carbon atoms, $R^2$ contains from 1 to 9 carbon atoms.

Starting from a perhalofluoroxy compound containing chlorine, radicals $R^3$ derived from $R_x$ are formed, wherein $R_x$ having at least two carbon atoms has lost one or more carbon atoms and/or $R_x$ having at least three carbon atoms has undergone a re-arrangement and one or more chlorine atoms of $R_x$ have been substituted by fluorine atoms. More commonly, radical $R^3$ is a radical $R^4$ containing a lower number of carbon atoms with respect to $R_x$ (wherefore when $R^4$ contains from 2 to 10 carbon atoms, $R^4$ contains from 1 to 9 carbon atoms) and in which one or more chlorine atoms have been substituted by fluorine atoms.

Starting from a perfluorofluoroxy compound, the obtainable telomers, depending on the utilized operative modalities, are the following (in each of the telomers, the monomeric unit $CF_2—CFCl$ has been schematically represented by letter (M):

$$R_x—CF_2—O—(M)_n—F \quad (A)$$

in which $R_x$ is the same as defined above, and "n" ranges from 1 to 20.

$$R_x—CF_2—O—(M)_n—O—CF_2—R_x \quad (B)$$

$$R_x—(M)_n—F \quad (C)$$

$$R_x—(M)_n—R_x \quad (D)$$

$$R_x—CF_2—O—(M)_n—R_x \quad (E)$$

$$R_x—O—(M)_n—F \quad (F)$$

$$R_x—O—(M)_n—O—CF_2—R_x \quad (G)$$

$$R_x—O—(M)_n—R_x \quad (H)$$

$$R_x—CF_2—(M)_n—F \quad (I)$$

$$R_x—CF_2—(M)_n—O—CF_2—R_x \quad (J)$$

$$R_x—CF_2—(M)_n—R_x \quad (K)$$

$$R^1—O—(M)_n—OCF_2—R_x \quad (L)$$

in which $R^1$ is a radical derived from $R_x$, in which $R_x$ having at least two carbon atoms has lost one or more carbon atoms and/or $R_x$ having at least 3 carbon atoms has undergone a re-arrangement:

$$R^1—O—(M)_n—R_x \quad (N)$$

$$R^1—(M)_n—F \quad (O)$$

$$CF_3—O—(M)_n—F \quad (P)$$

$$F—(M)_n—F \quad (Q)$$

$$CF_3—O—(M)_n—O—CF_3 \quad (R)$$

$$R_x—CF_2—O—(M)_n—Cl \quad (A')$$

$$R_x—(M)_n—Cl \quad (C')$$

$$R_x—O—(M)_n—Cl \quad (F')$$

$$R_x—CF_2—(M)_n—Cl \quad (I')$$

$$R^1—(M)_n—Cl \quad (O')$$

$$CF_3—O—(M)_n—Cl \quad (P')$$

$$F—(M)_n—Cl \quad (Q')$$

$$Cl—(M)_n—Cl \quad (Q'')$$

Preferably, "n" ranges from 1 to 10.

The distribution of monomeric units $—CF_2—CFCl$ is at random, i.e.: they can be linked both in a head-to-head and in head-to-tail arrangement.

Telomers (A'), (C'), (F'), (I'), (O') and (R') are new compounds.

In the obtained telomer mixtures, little amounts of telomers having different formula than the indicated ones may be present.

It is to be borne in mind that in the indicated telomer formulas, (M) may be either $(CF_2—CFCl)$ or $(CFCl—CF_2)$. Thus, to telomers $R_x—CF_2—O—(M)_n—F$ (A), two series of products are corresponding, which are represented by formulas:

1) $R_x—CF_2—O—(CF_2—CFCl)_n—F \quad (A_1)$ in which end group $R_x—CF_2—O—$ is bound to group $CF_2$ while end group F is bound to group CFCl, independently of the linkage of the intermediate monomeric units, when n is higher than 2.

2) $R_x$—$CF_2$—O—(CFCl—$CF_2$)$_n$—F    (A$_2$)

in which end group $R_x$—$CF_2$—O— is bound to group CFCl while end group F is bound to group $CF_2$, independently of the linkage of the intermediate monomeric units, when n is higher than 2.

When $R_x$ is a perhaloalkylpolyethereal radical, it preferably contains two oxygen atoms.

Preferably, $R_x$ contains from 1 to 4 carbon atoms.

Most preferred telogens are $CF_3OF$ and the ones of formula $R_x$—$CF_2OF$, wherein $R_x$ is a perfluoroalkyl radical containing from 1 to 4 carbon atoms.

When it is operated under such conditions as to increase the proportion of telomers having —F end groups, telomers of formula (A), (B), (C), (D), (E), (F), (I), (J) and (Q) are prevailingly obtained.

When it is operated under such conditions as to obtain mixtures of telomers containing species having —Cl end groups, prevailingly telomers (A), (B), (Q), (A'), (Q'), (Q'') and, in lesser amounts, telomers (F), (P), (C), (E), (G), (F') and (C') are obtained.

The telomer mixtures obtained through the process of the present invention are useful in particular as hydraulic fluids and service fluids.

By fractionated distillation of the mixtures it is possible to obtain fractions prevailingly consisting of telomers having a defined value of "n".

Among the fluoroxy compounds utilizable in the process of the present invention, the following can be cited:
fluoroxy trifluoromethane
fluoroxy pentafluoroethane
1-fluoroxy heptafluoropropane
1-fluoroxy nonafluorobutane
1-fluoroxy 2-chlorotetrafluoroethane
1-fluoroxy 2,2-dichlorotrifluoroethane
fluoroxy heptafluoroisopropane
fluoroxy nonafluoroisobutane
fluoroxy nonafluoro-ter.butane
1-fluoroxy-2-perfluoro-n.propoxy-hexafluoropropane
1-fluoroxy-2-perfluoromethoxy-hexafluoropropane
1-fluoroxy-2-perfluoroethoxy-hexafluoropropane and
1-fluoroxy-3-chlorohexafluoro-n.propane.

When $CF_3CF_2OF$ is used as a telogen, the obtained telomer mixture can be composed, depending on the operative conditions, by the following species:

| | |
|---|---|
| $F(M)_nF$ | (Ia) |
| $F(M)_nOCF_2CF_3$ | (IIa) |
| $CF_3CF_2O(M)_n$—$OCF_2CF_3$ | (IIIa) |
| $CF_3(M)_n$—F | (IVa) |
| $CF_3(M)_n$—$OCF_2CF_3$ | (Va) |
| $CF_3O(M)_n$—$OCF_2CF_3$ | (VIa) |
| $CF_3CF_2$—$(M)_n$—F | (VIIa) |
| $CF_3CF_2(M)_n$—$OCF_2CF_3$ | (VIIIa) |
| $CF_3O(M)_nF$ | (IXa) |
| $CF_3$—$(M)_n$—$CF_3$ | (Xa) |
| F—$(M)_n$—Cl | (I'a) |
| Cl—$(M)_n$Cl | (I''a) |

| | |
|---|---|
| $CF_3CF_2O(M)_n$—Cl | (II'a) |
| $CF_3(M)_n$—Cl | (IV'a) |
| $CF_3O$—$(M)_n$—Cl | (IX'a) |

Species (II'a), (IV'a) and (IX'a) are new telomers.

Starting from $CF_3$—$CF_2OF$ and directing the reaction towards the obtainment of telomers with an increased proportion of —F end groups, telomers (Ia), (IIa), (IIIa), (IVa), (Va) and (VIa) are prevailingly obtained.

Starting from $CF_3$—$CF_2OF$ and directing the reaction towards the obtainment of telomer mixtures containing species having —Cl end groups, telomers (Ia), (IIa), (IIIa), (IVa), (Va), (VIa), (IXa), (I'a), (I''a), (II'a), (IV'a) and (IX'a) are prevailingly obtained.

When $CF_3OF$ is used as a telogen, the mixture of obtained telomers can be composed, depending on the operative conditions, of the following species:

| | |
|---|---|
| $F(M)_nF$ | (Ia) |
| $CF_3O(M)_nF$ | (IXa) |
| $CF_3O(M)_nOCF_3$ | (IIIb) |
| $F(M)_nCl$ | (Ib) |
| $CF_3O(M)_nCl$ | (IIb) |
| $Cl(M)_nCl$ | (I'a) |

Species (IIb) are new telomers.

Starting from $CF_3OF$ and directing the reaction towards the obtainment of telomers having an increased proportion of —F end groups, telomers (Ia) and (IXa) are prevailingly obtained.

Starting from $CF_3OF$ and directing the reaction toward the obtainment of telomer mixtures containing telomers having —Cl end groups, telomers (Ia), (Ib) and (IIb) are prevailingly obtained.

The main advantages of the present invention are summarized hereinafter. It is possible to vary, over a wide range, the distribution and the nature of the end groups which are present in the obtained telomeric species and, in certain limits, the telomerization degree, so obtaining a wide range of products having different physical and chemical properties and capable of meeting various applicative requirements. In particular, it is possible to obtain mixtures of telomers having an increased content of —F end groups or telomer mixtures containing species having —Cl end groups.

The following examples are given for merely illustrative purposes and are not to be considered as to be a limitation of the present invention.

EXAMPLE 1

A flow of 0.32N liters/hour of $CF_3$—$CF_2OF$, 0.88N liters/hour of elemental fluorine and 30N liters/hour of nitrogen was made to continuously bubble into 204 g of liquid chlorotrifluoroethylene (CTFE), cooled to $-72°$ C., in a glass reactor having a 0.5 liter volume and equipped with reflux cooler, thermometer and mechanical stirrer.

After 5 hours, the reaction was stopped and the unreacted CTFE was distilled off.

59 g of product, with a yield of about 36.9 g of telomers per N liter of gaseous $CF_3—CF_2OF$ was obtained.

By gas-chromatography, the composition was evaluated in values of "n". The product was furtherly examined via gas-mass analysis by means of a capillary column SE-52. Furthermore, $^{19}F$ N.M.R. spectra were carried out by means of a BRUKER instrument AM 300, dissolving the samples in $CDCl_3$.

Compounds (Ia), (IIa), (IIIa), (IVa), (Va), (VIa), (VIIa), (VIIIa), (IXa), and (Xa) were present. Species (Ia), (IIa) and (IIIa) represented about 83% by weight of the mixture while species (Ia) represented about 45% of it.

The share, in per cent by weight, of the species containing F end groups (Ia, IIa, IVa and IXa) was higher, in the aggregate, than 84% by weight of all the species which were present.

In the product with "n" equal to 2, also the following compounds were present:

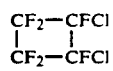  (I)

and

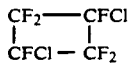  (II)

The gas-chromatographic distribution of the values of "n" proved to be the following:

| value of "n" | area % |
| --- | --- |
| 1 | 14 |
| 2 | 57.4 |
| 3 | 6.5 |
| 4 | 9.1 |
| 5 | 6.7 |
| 6 | 3.7 |
| 7 | 1.7 |
| 8 | 0.7 |

EXAMPLE 2

Following the procedure of example 1, 0.32N liters/hour of $CF_3—CF_2OF$, 0.88N liters/hour of elemental fluorine and 3.0N liters/hour of $N_2$ were made to bubble into 187 g of CTFE, at $-72°$ C., for 3 hours. After having distilled off the unreacted CTFE, 3.8 g of product were obtained.

Compounds Ia, IIa, IIIa, IVa, Va, VIa, IXa, I'a, I''a, II'a, IV'a and IX'a were present. Species Ia, I'a, I''a and II'a represented about 90% of the mixture. The terms having a value of "n" ranging from 3 to 6 corresponded to 70% of the total. The elemental analysis of the product indicated that the Cl/F weight ratio was equal to 0.7.

EXAMPLE 3

Following the procedure of example 1, a flow of 0.85N liters/hour of $CF_3—CF_2OF$, 0.35N liters/hour of $F_2$ and 10N liters/hour of $N_2$ was made to bubble into 184 g of liquid CTFE, at $-72°$ C., for 5 hours. After having distilled off the unreacted CTFE, 86.7 g of product were obtained; the molar yield with respect to $CF_3—CF_2OF$ was of about 99%, corresponding to about 20.4 g of telomers per liter of gaseous $CF_3—CF_2OF$.

The product resulted to be composed of telomeric species Ia, IIa, IIIa, IVa, Va, VIa, VIIa, VIIIa, IXa and Xa, of which species from Ia to IIIa represented more than 80% of the mixture. The share of all the species containing F end groups (Ia, IIa, IVa and IXa) exceeded, in the aggregate, 79% by weight of all the present species.

The fraction with "n" equal to 2 contained also compounds (I) and (II), the formula of which has been indicated in example 1.

The gas-chromatographic analyses revealed that the product consisted of terms having the values of "n" indicated hereinbelow:

| value of "n" | area % |
| --- | --- |
| 1 | 19.1 |
| 2 | 22 |
| 3 | 15.4 |
| 4 | 25.8 |
| 5 | 12 |
| 6 | 4.4 |
| 7 | 1.4 |
| 8 | 0.3 |

EXAMPLE 4

A comparative test (with respect to example 3) is here reported, in which it was operated in the absence of elemental fluorine.

Following the procedure of example 1, 0.85N liters/hour of $CF_3—CF_2OF$ and 10N liters/hour of nitrogen were made to bubble into 184 g of CTFE at $-72°$ C., for 5 hours. After removal of the unreacted CTFE, 75.2 g of product were obtained with a molar yield of about 80% with respect to $CF_3—CF_2OF$. Compounds Ia, IIa, IIIa, IVa, Va, VIa, VIIa, VIIIa, IXa, Xa were present. Species from Ia to IIIa represented about 80% of the mixture. The share of all the species containing F end groups (Ia, IIa, IVa and IXa) was lower, in the aggregate, than 69% by weight of the present species.

The terms with values of "n" ranging from 2 to 6 were corresponding to about 87% of the total.

EXAMPLE 5

Following the procedure of example 1, 1.2N liters/hour of $CF_3OF$, 0.6N liters/hour of $F_2$ and 2.5N liters/hour of $N_2$ were made to bubble into 200 g of liquid CTFE at $-60°$ C., for 5 hours. After the unreacted CTFE was distilled off, 46 g of product were obtained, with a yield of about 7.7 g of telomers per liter of gaseous $CF_3OF$. Compounds Ia, Ib, IIb, I''a, IIIb and IXa were present.

We claim:

1. A process for preparing chlorotrifluoroethylene telomers which comprises reacting chlorotrifluoroethylene, elemental fluoride and a perhalofluoroxy compound of formula $CF_3OF$ or $R_x—CF_2—OF$, in which $R_x$ represents a perhalogenated alkyl radical, a perhaloalkylmonoethereal radical or a perhaloalkylpolyethereal radical, either straight or branched, having from 1 to 10 carbon atoms and containing fluorine atoms or fluorine and chlorine atoms, at a temperature ranging from $-100°$ to $+40°$ C.; the perhalofluoroxy compound and the elemental fluorine being fed to the reaction medium after being diluted in a gas which is inert under the reaction conditions, the ratio, in N liters/hour, between fluorine and perhalofluoroxy compound ranging from 0.1 to 20 and the ratio $$\frac{\text{perhalofluoroxy compound + fluorine}}{\text{inert gas}}$$

in N liters/hour, ranging from 0.01 to 1.

2. The process according to claim 1, wherein telomer mixtures having an increased content of —F end groups are obtained by using a fluorine/perhalofluoroxy compound ratio ranging from 0.1 to 10 and a $$\frac{\text{perhalofluoroxy compound + fluorine}}{\text{inert gas}}$$

ratio ranging from 0.01 to 0.50.

3. The process according to claim 2, wherein the reaction is carried out at a temperature ranging from −100° to −40° C.

4. The process according to claim 1 wherein telomer mixtures containing species having —Cl end groups are obtained by using a fluorine/perhalofluoroxy compound ratio ranging from 2 to 20 and a $$\frac{\text{perhalofluoroxy compound + fluorine}}{\text{inert gas}}$$

ratio ranging from 0.3 to 1.

5. The process according to claim 4, wherein the reaction is carried out at a temperature ranging from −75° to +40° C.

6. The process according to claim 1, wherein a stream of gaseous or liquid perhalofluoroxy compound and of gaseous fluorine, both diluted in the inert gas, is fed to a reactor containing chlorotrifluoroethylene in the liquid state or dissolved in a solvent.

7. The process according to claim 6, wherein the perhalofluoroxy compound is fed in the gaseous state.

8. The process according to claim 6, wherein the solvent for chlorotrifluoroethylene is a chlorofluorocarbon.

9. The process according to claim 1, wherein when $R_x$ is a perhaloalkylpolyethereal radical containing two oxygen atoms.

10. The process according to claim 1, wherein $R_x$ contains from 1 to 4 carbon atoms.

11. The process according to claim 1, wherein the perhalofluoroxy compound is $CF_3OF$ or a compound of the formula $R_x$—$CF_2OF$ wherein $R_x$ is a perfluoroalkyl radical containing from 1 to 4 carbon atoms.

* * * * *